US006472192B1

(12) United States Patent
Schulz et al.

(10) Patent No.: US 6,472,192 B1
(45) Date of Patent: Oct. 29, 2002

(54) CYCLODEXTRIN GLYCOSYL TRANSFERASES FOR PRODUCING γ-CYCLODEXTRIN

(75) Inventors: Georg E. Schulz, Denzlingen; Goetz Parsiegla, Freiburg, both of (DE)

(73) Assignee: Consortium für Elektrochemische Industrie GmbH, München (DE)

( * ) Notice: Subject to any disclaimer, the term of this patent is extended or adjusted under 35 U.S.C. 154(b) by 0 days.

(21) Appl. No.: 09/430,702

(22) Filed: Oct. 29, 1999

Related U.S. Application Data

(63) Continuation-in-part of application No. 08/816,317, filed on Mar. 13, 1997.

(30) Foreign Application Priority Data

Apr. 18, 1996  (DE) .......................................... 196 15 336

(51) Int. Cl.[7] .............................. C12N 9/10; C12N 1/00; C12P 21/04; C08H 1/00; C07H 21/04
(52) U.S. Cl. ...................... 435/193; 435/69.8; 435/832; 435/252.3; 435/320.1; 435/325; 530/412; 536/23.2; 536/23.7
(58) Field of Search .............................. 435/193, 69.8, 435/832, 252.3, 320.1, 325; 530/412; 536/23.2, 23.7

(56) References Cited

U.S. PATENT DOCUMENTS

| | | | |
|---|---|---|---|
| 4,808,232 A | 2/1989 | Beesley | 127/46.3 |
| 4,822,874 A | 4/1989 | Schmid et al. | 536/102 |
| 5,376,537 A | 12/1994 | Cami et al. | 435/101 |
| 5,409,824 A | 4/1995 | Schmid | 435/193 |
| 5,474,917 A | 12/1995 | Schulz et al. | 435/97 |

FOREIGN PATENT DOCUMENTS

| | | |
|---|---|---|
| DE | 4009822 | 10/1991 |
| DE | 4324650 | 1/1995 |
| EP | 0291067 | 11/1988 |
| EP | 0481513 | 4/1992 |
| EP | 0614571 | 9/1994 |
| EP | 0630567 | 12/1994 |
| WO | WO91/14770 | 10/1991 |
| WO | WO96/33267 | 10/1996 |

OTHER PUBLICATIONS

J. Ferm. Bioeng. (1990) 70 (3), p. 150–154 "Purification of Cyclodextrin Glysolyltransferase from Bacilus sp. AL–6", by Fujita et al.

Biochemistry (1994) 33 (33), pp. 9929–9936, Four Aromatic Residues in the Active Center of Cyclodextrin Glucanotransferase from Alkalophilic Bacillus sp. 1011: Effects of Replacements on Substrate Binding and Cyclization Characteristics, by Nakamura et al.

Biochemistry (1995) 34 (10), pp. 3368–3376, "Site–Directed Mutations in Tyrosine 195 of Cyclodextrin Glycosyltransferase from *Bacillus circulans* Strain 251 Affect Activity and Product Specificity", by Penninga et al.

Cold Spring Harbor Lab., Cold Spring Harbor, NY, pp. 121–129, "Experiments in Molecular Genetics", by Jeffrey H. Miller.

Proc. Natl. Acad. Sci. USA, pp. 5463–5467, "DNA Sequencing With Chain–Terminating Inhibitors", by Sanger et al.

Technique (1989) 1 (1). pp. 11–15, Method for Random Mutagenesis of a Defined DNA Segment Using a Modified Polymerase Chain Reaction, by Leung et al.

Current Protocols In Molecular Biology, pp. 2.4.1–2.4.2, "Preparation of Genomic DNA from Bacteria", by Ausubel et al.

Promega 1992–93 Catalog 150, pp. 138–139, "Revolutions in Science", Molecular Biology/Reagent System.

Ann. Rev. Genet., 1985, pp. 423–462, "In Vitro Mutagenesis", by Michael Smith vol. 19.

Journal of Fermentation and Bioengineering, vol. 70, No. 3, 190–192, 1990, "Some Factors Affecting the Formation of γ–Cyclodextrin Using Cyclodextrin Glycosyltransferase from Bacillus sp. AL–6", by Tomita et al.

CA 107:57466, Horikoshi et al., Feb. 3, 1987, Microbial Production of δ CD Synthetose and its use in the manufacture of δ CD.

Current Protocols in Molecular Biology, pp. 8.1.1–8.1.6, "Oligonucleotide–Directed Mutagenesis Without Phenotypic Selection", by Ausubel et al.

Appl. Microgiol. Biotechnol (1990) 33:542–546, Molecular Cloning, Nucleotide Sequence and Expression in *Escherichia coli* of the β–Cyclodextrin Glycosyltransferase Gene from *Bacillus Circulans* Strain No. 8, by Nitschke et al.

Cold Spring Harbor Lab., Cold Spring Harbor, NY, pp. 86–92, Molecular Cloning "Large Scale Isolation of Plasmid DNA" by T. Maniatis et al.

Nucl. Acids. Res. (1986), 14, p. 9679–9698, "Inhibition of restriction endonuclease Nci I cleavage by phosphorothioate groups and its application to oligonucleotide–directed mutagenesis", by Nakamaye and Eckstein.

(List continued on next page.)

*Primary Examiner*—Tekchand Saidha
(74) *Attorney, Agent, or Firm*—Collard & Roe, P.C.

(57) ABSTRACT

CGTases, which, when converting starch or starch-like substrates to CD, produce γ-CD to an increased extent and still exhibit at least 60% of the specific total CGTase activity of the starting CGTase which was used for preparing the enzyme concerned. The amino acid sequences differ from the amino acid sequences of known CGTases by the deletion of from 3 to 8 amino acids from the region from amino acid position 155 up to and including amino acid position 195, where position 1 of the protein sequence is the beginning of the signal peptide of the CGTase and the deletion brings about the increase in the γ-CGTase activity of the protein.

6 Claims, 5 Drawing Sheets

OTHER PUBLICATIONS

Nuc. Acids. Res. (1988), 16, pp. 791–802, 5'–3' Exonucleases in phosphorothioate–based oligonucleotide–directed mutagenesis, by John R. Sayers et al.

Eur. J. Biochem., pp. 177–185 (1990), "Biochemical and genetic analysis of a maltopentaose–producing amylase from an alkaliphilic Gram–positive bacterium", by Anton Candussio et al. vol. 191.

Anal. Biochem. (1976), 72, p. 248 "A Rapid and Sensitive Method for the Quantitation of Microgram Quantities of Protein Utilizing the Principle of Protein–Dye Binding", by M. Bradford.

Cold Spring Harbor Lab., Cold Spring Harbor, NY, p. 68, "Propagation and Maintenance of Bacterial Strains and Viruses", by Maniatis et al.

Cold Spring Harbor Lab., Cold Spring Harbor, NY, pp. 249–251, "Transformation of *Escherichia coli* by Plasmid DNA", by Maniatis et al.

Derwent Abstract 95–100943 (XP002034113).

Derwent Abstract 93–308317 (XP002034114) JP 5219948, Uozumi, T., issued Aug. 31, 1993.

Derwent Abstract 93–103608 (XP002034115) JP 5041985, Oji Com Starch G. Ltd., issued Feb. 23, 1993.

Biotechnology and Applied Biochemistry 12, 387–396 (1990), "Effects of Modifications at the C–Terminus of Cyclomaltodextrin Glucanotransferase from *Bacillus circulans var. alkalophilus* on Catalytic Activity", by Hellman et al.

Journal of Biotechnology, 32 (1994) 283–288, "Replacement of an amino acid residue of cyclodextrin glucanotransferase of *Bacillus ohbensis* doubles the production of γ–cyclodextrin", by Sin et al.

Journal of Fermentation and Bioengineering vol. 74, No. 6, 345–351, 1992 "Cloning and Sequencing of the Gene Encoding Cyclodextrin Glucanotransferase from Bacillus sp. KC201", by Kitamoto et al.

Derwent Abstract No. 95–100943.

Reeck et al. (1987) "Homology" in Proteins and Nucleic Acids: A Terminology Muddle and a Way out of it. Cell 50:667.*

* cited by examiner

```
                                                                              SEQ ID NO
Bacillus sp. 1-1      120...▓▓▓kt▓pyy▓n(g▓▓dr▓ma▓▓sng▓vim▓▓▓▓▓let-169            1
Bac. ohbensis         120...▓▓▓rt▓pfy▓dfs▓▓rnd▓▓sng▓vim▓▓▓▓▓let-169            2
Bac. circulans 88     132...▓▓ki▓hyf▓kma▓qm▓it▓▓akg▓ivi▓a▓▓▓▓et-181             3
Paenibac. macerans    125...▓▓qt▓af▓dfa▓▓qn▓d▓▓ahg▓vvi▓a▓▓▓▓rd-174              4
Thermoanaerob. sp.    126...▓f▓kp▓pff▓sft▓▓qn▓ia▓▓aha▓vii▓▓▓▓▓et-175             5

Bacillus sp. 1-1      170-npny▓▓▓si▓dn▓▓▓ln▓▓▓qnl▓▓▓tn▓▓sy▓dis▓▓▓▓...219        1
Bac. ohbensis         170-dpsy▓▓▓av▓nd▓▓▓▓▓pnn▓▓▓tn▓▓sy▓dis▓▓▓▓...219           2
Bac. circulans 83     182-dtsfa▓▓▓l▓n▓tv▓▓▓sngy▓▓▓n▓▓sn▓▓slhg▓▓▓▓...231         3
Paenibac. macerans    175-npgfa▓▓▓gm▓ns▓▓▓▓▓cagi▓▓▓tn▓▓r▓idg▓▓▓▓...224         4
Thermoanaerob. sp.    176-dptyd▓▓▓r▓▓dn▓v▓▓▓▓▓tngy▓▓▓tn▓▓sy▓dn▓▓▓▓...225       5
```

*Figure 1: Comparison of the amino acid sequences of five CGTases. The conserved residues are shadowed. The eight amino acid residues underlined and in bold print are in each case relevant for modifying the product specificity.*

| SEQ ID NO: | Line in table 1 | number of del. aminoacids | Bacillus sp. 1-1 - CGTase from position 165 to 174: aminoacid sequence from wildtype and deletion mutants | | | | | | | | | |
|---|---|---|---|---|---|---|---|---|---|---|---|---|
| 21 | - | 0 (wildtype) | - | P | A | L | E | T | N | P | N | - |
| 22 | 1 | 3 | - | P | A | L | E | · | · | · | N | V |
| 23 | 2 | 3 | - | P | A | L | · | T | · | P | Y | V |
| 24 | 3 | 4 | - | P | A | L | · | · | · | · | Y | V |
| 25 | 4 | 5 | - | P | A | L | · | · | · | · | Y | V |
| 26 | 5 | 6 | - | P | A | · | · | · | · | · | Y | V |
| 27 | 6 | 7 | - | P | · | · | · | · | · | · | · | V |
| 28 | 7 | 5 | - | P | · | L | · | T | · | P | · | V |
| 29 | 8 | 8 | - | P | · | · | · | · | · | · | · | V |

Fig. 2:

| SEQ ID NO: | Line in table 1 | number of del. aminoacids | Thermoanaerobacter CGTase from position 171 to 180: aminoacid sequence from wildtype and deletion mutants | | | | | | | | | |
|---|---|---|---|---|---|---|---|---|---|---|---|---|
| 38 | - | 0 (wildtype) | - | P | A | S | E | T | D | P | T | Y | G |
| 39 | 12 | 3 | - | P | A | S | E | . | . | . | T | Y | G |
| 40 | 13 | 3 | - | P | A | S | . | T | . | P | . | Y | G |
| 41 | 14 | 5 | - | P | A | S | . | . | . | . | . | Y | G |

Fig. 3:

| SEQ ID NO | Line in table 1 | No. of del. aminoacids | sequences of oligonucleotides used for deletion mutagenesis |
|---|---|---|---|
| 30 | 1 | 3 | 5'- T C A C C G G C A C T T G A A A A C T A T G T T T G A A A A T -3' |
| 31 | 2 | 3 | 5'- T C C A C C C G G C A C T T A C G C T T A T G T G A A A A T -3' |
| 32 | 3 | 4 | 5'- T C C A T C C A C C C G G C A C T T T A A C T T A T G T T G A A A A T -3' |
| 33 | 4 | 5 | 5'- T C C A T T C C A C C C G G C A C T T T A T G T T T G A A A A T G G G -3' |
| 34 | 5 | 6 | 5'- C A T T C A C C C G G C A C C G G C A T A T G T T G A A A A T G G G -3' |
| 35 | 6 | 7 | 5'- C A T C A C C C G C C A C C G G C A G T C C T T G T T G A A A A T G G C G -3' |
| 36 | 7 | 5 | 5'- T C A C C C G C T C A C G C C T T G T T G A A A A T G G G -3' |
| 37 | 8 | 8 | 5'- A A T C A T T C A C C G G T T C A C C G G T T G A A A A T G G G C G -3' |

FIG. 4

| SEQ ID NO | Line in table 1 | No. of del. aminoacids | sequences of oligonucleotides used for deletion mutagenesis |
|---|---|---|---|
| 42 | 12 | 3 | 5'- T C T C C T G C A T C A G A G A C C T A T G G G G A A A A T -3' |
| 43 | 13 | 3 | 5'- T C T C C T G C A T C A A C A C C T T A T G G G G A A A A T -3' |
| 44 | 14 | 5 | 5'- A C A T C T C C T G C A T C A T C A T A T G G G A A A A T G G T -3' |

FIG. 5:

CYCLODEXTRIN GLYCOSYL TRANSFERASES FOR PRODUCING γ-CYCLODEXTRIN

CROSS-REFERENCE TO RELATED APPLICATION

This is a Continuation-In-Part patent application of copending parent U.S. patent application Ser. No. 08/816,317 filed Mar. 13, 1997.

BACKGROUND OF THE INVENTION

1. Field of the Invention

The present invention relates to cyclodextrin glycosyl transferases (CGTases) EC 2.4.1.19 for producing γ-cyclodextrin, to processes for preparing γ-cyclodextrin glycosyl transferases, and to their use.

2. The Prior Art

As a rule, cyclodextrins are prepared from starch or starch-like substrates. In these preparations, CGTases are used to convert starch enzymatically into cyclodextrin (CD). For thermodynamic reasons, the starch is mainly converted into β-CD, independently of the CGTase used for the reaction, if the reaction is carried out until the thermodynamic equilibrium is reached (maximum CD yield). However, in the initial phase, at the beginning of the starch conversion reaction, the enzymes which are used for the conversion differ in the composition of the primary product mixture. α- β- or γ-CGTases are differentiated depending upon the product, α, β-, or γ-CD, which is chiefly formed by the enzyme in this initial phase.

These enzymes, which are suitable, and have also already been used, for the industrial production of CD, have hitherto only been detected in bacteria. α-CGTases have hitherto only been identified in *Bacillus macerans, Bacillus stearothermophilus* and *Klebsiella oxytoca*. β-CGTases have been detected, for example, in *Bacillus circulans, Bacillus megaterium, Bacillus ohbensis*, Micrococcus sp. and alkalophilic Bacillae which have not been precisely classified taxonomically, such as Bacillus sp. 38-2, 17-1, 1011 or 1-1. Naturally occurring enzymes having an initially high γ-CD-forming activity have been reported in *Bacillus subtilis* 313, Bacillus sp. A1-6 and Bacillus sp. 290-3.

Since the CGTases which are used in the industrial preparation of cyclodextrins always yield mixtures of several cyclodextrins when converting starch into cyclodextrins, various processes have been developed for isolating pure cyclodextrins (α, β or γ). These are described below:

Defined CDs can be separated out chromatographically from the product mixtures, e.g. on the basis of differences in their molecular weights (described, for example, in U.S. Pat. No. 4,808,232).

As a rule, when starch is converted enzymatically into cyclodextrins, complexing agents are added which only react with one defined CD and with this CD form an insoluble complex, for example, which can then be separated out from the reaction mixture by physical means. Subsequently, the complex is resolved and the homogeneous CD is isolated (described, for example, in EP 0291067).

When a γ-CGTase is used, the product composition can be displaced in the γ-CD direction by adding an organic solvent, such as ethanol, to the reaction mixture (*J. Ferrm. Bioeng.* (1990) 70 (3), pp. 150–154).

In each of the processes, those CGTases are optimally used which possess an initial product formation preference which is as high as possible for the CD which is to be prepared in pure form.

The specificity of the previously known α- and β-CGTases is adequate for industrial production of the corresponding cyclodextrins. By contrast, none of the known, naturally occurring γ-CGTases possesses a product specificity which permits a comparable industrial production of γ-CD.

In order to prepare γ-CD, therefore, it was proposed, in CA 115:157165, that α- and/or β-Cyclodextrins be converted enzymatically into γ-CD by adding the γ-CD-specific complexing agent glycosyl glycyrrhizin, maltose and a CGTase.

Another option for preparing γ-CD consists in increasing the γ-CD specificity of β-CGTase, by means of exchanging defined amino acid residues, to such a degree that the mutagenized enzyme produces γ-CD to an increased extent and can consequently be used for preparing γ-CD on an industrial scale. Appropriate mutations are known and described, for example, in DE 43 24 650 A1 (corresponds to U.S. Pat. No. 5,474,917), *Biochemistry* (1994) 33 (33), pp. 9929–9936, *Biochemistry* (1995) 34 (10), pp. 3368–3376 and *J. Biotech*. (1994) 32, pp. 283–288.

Such CGTase derivatives, which have been produced by mutagenizing β-CGTases, possess an increased specificity for γ-CD and are consequently, on the basis of their product spectra, suited, in principle, for the industrial preparation of γ-CD. However, a disadvantage is that the specific activities of the starting enzymes which are used for the mutagenesis are reduced by introducing the relevant mutations. In dependence on the amino acid residues which are introduced, mutated enzymes having an increased specificity for γ-CD only possess between 25% and 50% of the CD-forming activity of the starting enzyme (*Biochemistry* (1994) 33 (33), pp. 9929–9936, *Biochemistry* (1995) 34 (10), pp. 3368–3376).

SUMMARY OF THE INVENTION

It is an object of the present invention to provide cyclodextrin glycosyl transferases (CGTases) which, when converting starch or starch-like substrates into CD, produce γ-CD to an increased extent and which still exhibit at least 60% of the specific total CGTase activity of the starting CGTase which was used for preparing the enzyme concerned.

An additional object of the present invention is to provide processes for preparing the said CGTases.

A further object of the present invention is to provide a process for producing γ-CD.

The first-mentioned object is achieved by CGTases whose amino acid sequence differs from the amino acid sequence of wild-type CGTases by the deletion of from 3 to 8 amino acids in the region from amino acid position 155 up to and including amino acid position 195, where position 1 of the protein sequence is the beginning of the signal peptide of the CGTase and the deletion increases the γ-CGTase activity of the protein.

Within the meaning of the invention, increases in the γ-CGTase activity is understood to mean that the quotient $$\frac{\text{quantity of } \gamma\text{-CD formed}}{(\text{quantity of } \alpha\text{-CD formed} + \text{quantity of } \beta\text{-CD formed})}$$

becomes greater in the product mixture which arises when starch or starch-like substrates are reacted with CGTases.

Preferably, the amino acid sequences of CGTases according to the invention differ from the amino acid sequences of known CGTases by between three and eight amino acid residues being deleted in the region between amino acid position 155 and amino acid position 195 of their protein sequence, where position 1 of the protein sequence is the beginning of the signal peptide of the CGTase and the deletion increases the γ-CGTase activity of the protein.

Particularly preferably, the amino acid sequences of CGTases according to the invention differ from the amino acid sequences of known CGTases by five amino acid residues being deleted in the region between amino acid position 155 and amino acid position 195 of their protein sequence, where position 1 of the protein sequence is the beginning of the signal peptide of the CGTase and the deletion increases the γ-CGTase activity of the protein.

It also applies for each of the other amino acid positions mentioned in the application that position 1 of the protein sequence is the beginning of the signal peptide of the CGTase.

In addition, CGTases are in particular preferred whose amino acid sequences differ from the amino acid sequences of the CGTases specified in Table 1 and FIG. 1 at least by the deletion of the amino acid residues which are in each case printed in bold, with the remaining amino acid sequence of the respective CGTase according to the invention being homologous to the amino acid sequence of the CGTase specified in Table 1 and FIG. 1 to the extent that the sequence exhibits CGTase activity without the deletion according to the invention.

Examples of CGTases according to the invention are CGTases which are obtained from the CGTases listed in Table 1 and FIG. 1, or from other CGTases, by deleting individual amino acid residues in the region between the amino acid residues 155 and 195. CGTases are preferred in which from four to eight residues have been deleted from the said region. CGTases are particularly preferred in which the six amino acids marked by bold type in Table 1 and FIG. 1 have been deleted from the said region.

Further examples of CGTases according to the invention are enzymes from which the amino acids which are homologous to the amino acids specified in Table 1 and FIG. 1 have been deleted, with these enzymes exhibiting CGTase activity without the deletion according to the invention.

Further, examples of CGTases according to the invention are enzymes in which the amino acid residues which are in each case printed in bold in FIG. 1 have been deleted from the region between amino acid position 155 and amino acid position 195, with the remaining amino acid sequence of the CGTases according to the invention being homologous to the amino acid sequence of the CGTase from the microorganism which is in each case specified in FIG. 1 and Table 1 to the extent that the enzyme whose sequence does not contain the deletion according to the invention exhibits CGTase activity.

The between three and eight amino acid residues of (SEQ ID NO: 6–13) in Table 1 are these deleted portions found in (SEQ ID NO:3). The six amino acid residues of (SEQ ID NO:14) is that deleted portion found in (SEQ ID NO:2). The six amino acid residues of (SEQ ID NO:15) is that deleted portion found in (SEQ ID NO:3). The six amino acid residues of (SEQ ID NO:16) is that deleted portion found in (SEQ ID NO:4). The three and five amino acid residues of (SEQ ID NO:17–19) in Table 1 are these deleted portions found in (SEQ ID NO:5).

The CGTase protein of the invention has an amino acid sequence which differs from the amino acid sequences of the CGTases specified in FIG. 1 and Table 1 at least by the deletion of the amino acid residues which are selected from the group consisting of:

(SEQ ID NO:6) deleted from (SEQ ID NO:1);
(SEQ ID NO:7) deleted from (SEQ ID NO:1);
(SEQ ID NO:8) deleted from (SEQ ID NO:1);
(SEQ ID NO:9) deleted from (SEQ ID NO:1);
(SEQ ID NO:10) deleted from (SEQ ID NO:1);
(SEQ ID NO:11) deleted from (SEQ ID NO:1);
(SEQ ID NO:12) deleted from (SEQ ID NO:1);
(SEQ ID NO:13) deleted from (SEQ ID NO:1);
(SEQ ID NO:14) deleted from (SEQ ID NO:2);
(SEQ ID NO:15) deleted from (SEQ ID NO:3).;
(SEQ ID NO:16) deleted from (SEQ ID NO:4);
(SEQ ID NO:17) deleted from (SEQ ID NO:5);
(SEQ ID NO:18) deleted from (SEQ ID NO:5) and
(SEQ ID NO:19) deleted from (SEQ ID NO:5).

The remaining amino acid sequence of the CGTase according to the invention is homologous to the amino acid sequence of the CGTase from the microorganism which is in each case specified in FIG. 1 to the extent that the sequence exhibits CGTase activity without the deletion according to the invention.

Incorporated herewith are five references which publish the complete sequence of the five GCTases compared in FIG. 1 of the application. These five references are as follows: "Cloning and Nucleotide Sequence of a Thermostable Cyclodextrin Glycosyltransferase Gene from Thermoanaerobacter sp. ATCC 53627 and Its Expression in *Escherichia coli*", S. T. Jorgensen et al, *Biotechnology Letters*, Vol. 19, No. 10, October 1997, pages 1027–1031; "Cloning and Sequencing of a Cyclodextrin Glucanotransferase Gene from *Bacillus ohbensis* and Its Expression in *Escherichia coli*\*", Sin et al., *Applied Microbiology and Biotechnology* (1991) 35:600–605; "Highly Homologous Cyclodextrin Glycosyltransferases from *Bacillus circulans* Strain 8 and a Strain of *Bacillus licheniformis*", Bender, *Applied Microbiology and Biotechnology* (1990) 34:229–230; "Molecular Cloning, DNA Nucleotide Sequencing, and Expression in *Bacillus subtilis* Cells of the *Bacillus macerans* Cyclodextrin Glucanotransferase Gene", Takano, et al., *Journal of Bacteriology*, vol. 166, No. 3, June 1986, pages 1118–1122; and "Cloning and Nucleotide Sequence of a Cyclodextrin it Glycosyltransferase Gene from the Alkalophilic Bacillus 1-1", O. Huber and J. Szejtli (eds.), *Proceedings of the Fourth International Symposium* on *Cyclodextrins*, 71–76, ©1988 by Kluwer Academic Publishers. Please note that the published sequence of B. macerans (=*Paenibacillus macerans*) includes several errors and that the correct sequence must be taken from the printout of the Swissprot-Database, also enclosed. These sequences and the complete publications are herewith incorporated by reference into the present application. The word "region" can also be substituted by "amino acid sequence(s)" or "peptide" or "part of the CGTases".

To define "homologous", it can be stated that homologous amino acid residues are determined as follows: The amino acid sequence of a respective CGTase has to be compared with the five CGTases as shown in FIG. 1 using the computer program "pile up" (Wisconsin Package Version 10.0, Genetics Computer Group (GCG), Madison, Wis.). Using the present standard parameters, the program generates a multiple alignment of the six CGTase sequences. Amino acid residues which are located at the same position in such an alignment are called "homologous".

The wording "position 155 and 195" was chosen to solve the problem resulting from the different absolute position of defined homologous amino acids in different CGTases. According to the teaching of the present application, a region of 8 amino acids is essential for the invention. Deletion within these 8 amino acids results in a change of the product specificity of the CGTase. Just because the absolute position of these 8 amino acids is not the same in all CGTases, the present application defines a sequence region (positions 155 to 195) in which the 8 amino acids essential for the invention can be found. Thus by the wording used in the present application, the region essential for the present application is defined independently from the absolute position in a CGTase.

TABLE 1

| β-CGTase from | Position | Amino acid sequence | Deleted Amino Acid Residues | Line |
|---|---|---|---|---|
| Bacillus sp. 1-1 | 120 | (SEQ ID NO: 1) | TNP (SEQ ID NO: 6) | 1 |
| | | | E.N.N (SEQ ID NO: 7) | 2 |
| | | | ETNP (SEQ ID NO: 8) | 3 |
| | | | ETNPN (SEQ ID NO: 9) | 4 |
| | | | LETNPN (SEQ ID NO: 10) | 5 |
| | | | LETNPNY (SEQ ID NO: 11) | 6 |
| | | | A.E.N.NY (SEQ ID NO: 12) | 7 |
| | | | ALETNPNY (SEQ ID NO: 13) | 8 |
| Bacillus ohbensis | 120 | (SEQ ID NO: 2) | LETDPS (SEQ ID NO: 14) | 9 |
| Bacillus circulans #8 | 132 | (SEQ ID NO: 3) | METDTS (SEQ ID NO: 15) | 10 |
| Paenibacilllus macerans | 125 | (SEQ ID NO: 4) | DRDNPG (SEQ ID NO: 16) | 11 |
| Thermoanaerobacter sp. | 126 | (SEQ ID NO: 5) | TDP (SEQ ID NO: 17) | 12 |
| | | | E.D.T (SEQ ID NO: 18) | 13 |
| | | | ETDPT (SEQ ID NO: 19) | 14 |

Unexpectedly, the CGTases according to the invention possess a higher γ-CD specificity than that of the starting CGTases which were used for their preparation while, at the same time, the mutated enzyme only exhibits an insignificant reduction in specific total CGTase activity as compared with that of the starting CGTase.

When converting starch or starch-like substrates, the CGTases according to the invention consequently produce CDs in a product distribution in which the quotient of γ-CD and the sum of α-CD and β-CD is greater than the quotient of these products which is obtained when starch is converted using the respective unaltered starting CGTase.

The list shown in Table 1 and in FIG. 1 shows, using a few CGTases by way of example, the homologous amino acid sequence region which is generally present in CGTases and the six amino acid residues within this sequence region which are in each case relevant for modifying the product specificity.

The four amino acid sequences shown in FIG. 1 are the same respectively as the four amino acid sequences shown in Table 1.

The number of the first amino acid of each of the amino acid sequences depicted in Table 1 and in FIG. 1 is designated as the position, with the first amino acid of the signal peptide of the particular CGTase sequence having been counted as position 1. The corresponding sequence region can be found in all CGTases using well known standard methods. This can be done, for example, using known algorithms which calculate multiple sequence alignments. An example of a suitable computer algorithm is the "pileup" program from the commercially available Wisconsin Sequence Analysis package (Genetic Computer Group, Madison, Wisconsin) sequence analysis program.

By means of mutagenizing the depicted region in CGTases, enzymes according to the invention can be prepared from any CGTases using known standard methods, as explained, by way of example, in the present application. For this purpose, a gene encoding a CGTase is as a rule mutated in such a way that it then encodes a CGTase according to the invention.

The invention consequently also relates to processes for preparing mutated CGTase genes which encode CGTases according to the invention, wherein the DNA sequence of a gene encoding a starting CGTase is mutated, by means of mutagenesis methods which are known per se, such that the amino acid sequence in the region between amino acid positions 155 and 195, which is encoded by the DNA sequence of the mutated gene, differs from the amino acid sequence which is encoded by the DNA of the unmutated gene by the deletion of at least one amino acid residue.

Preferably, in the process according to the invention, the DNA sequence of a gene encoding a starting CGTase is mutated, by means of mutagenesis methods which are known per se, such that the amino acid sequence encoded by the DNA sequence of the mutated gene differs from the amino acid sequence encoded by the DNA of the unmutated gene by the deletion of from four to eight amino acid residues from the region between amino acid positions 155 and 195.

Particularly preferably, in the process according to the invention, the DNA sequence of a gene encoding a starting CGTase is mutated, by means of mutagenesis methods which are known per se, such that the amino acid sequence encoded by the DNA sequence of the mutated gene differs from the amino acid sequence encoded by the DNA of the unmutated gene by the deletion of six amino acid residues from the region between amino acid positions 155 and 195.

The invention furthermore relates to processes for preparing γ-CGTases, wherein at least one of the described DNA sequences is expressed in a microorganism.

The genes of all CGTases (starting CGTases) are suitable for preparing the CGTases according to the invention. While starting CGTases can be all naturally occurring CGTases, they can also be CGTases which are obtained by mutagenesis, for example those CGTases in which the product formation ratio has already been altered by another mutation which is not in accordance with the invention (e.g.: as in DE 43 24 650 A1, which corresponds to U.S. Pat. No. 5,474,917). Starting CGTases are preferably those CGTases in which the product formation ratio has already been altered by another mutation which is not in accordance with the invention (e.g.: as described in DE 43 24 650 A1).

The gene encoding a starting CGTase is isolated using known methods and the mutation according to the invention is introduced into the gene of the CGTase by "in-vivo" or "in-vitro" mutagenesis methods. These methods are likewise well known in the state of the art.

"In-vivo" mutagenesis methods are to be understood as being, in particular, those methods in which microorganisms which chromosomally and/or episomally contain a gene encoding a CGTase are mutagenized in a non-specific manner with a mutagen such as UV light, nitrosoguanidine or ethyl methyl sulfonate. Such a method is described, for example, by Miller J. H. in (1972) *Experiments in Molecular Genetics*; Cold Spring Harbor Laboratory; Cold Spring Harbor, N.Y.

Subsequently, known methods, such as sequence analysis in accordance with the chain termination method described by Sanger et al. in *PNAS* 74 (1977) 5463–5467 are used to identify mutants in which at least one codon of the CGTase gene, encoding an amino acid residue, has been deleted from the region between amino acid residues 155 and 195 of the corresponding CGTase.

Those mutants are preferably selected in accordance with the invention in which from four to eight codons have been deleted from the said region.

Mutants are particularly preferably selected in which six codons have been deleted, with those mutants once again preferably being selected in which the six codons have been deleted which encode the amino acid residues which are printed in bold in FIG. 1 or encode the amino acid residues which are homologous to these residues in other CGTases.

Within the meaning of the invention, "in-vitro" mutagenesis methods are to be understood as being those methods in which an isolated CGTase gene, or a fragment of a CGTase gene, is modified, in a manner known per se, such that a gene is produced which encodes a CGTase enzyme in which at least one codon of the CGTase gene, encoding one of the amino acid residues in the region between amino acid residues 155 and 195, has been deleted.

Mutants are preferred which have been modified such that from four to eight codons have been deleted in the said region. Mutants are particularly preferred which have been modified such that six codons have been deleted in the said region. In particular, mutants are particularly preferred which have been modified such that, in the said region, the six codons have been deleted which encode the amino acid residues which are printed in bold in FIG. 1 or encode the amino acid residues which are homologous to these residues in other CGTases.

The invention consequently also relates to DNA sequences which encode γ-CGTases according to the invention.

Examples of methods for "in-vitro" mutagenesis which are known from the state of the art are specific (BioTechniques (1992) 13 (3), pp. 342–346) or non-specific (Technique (1989) 1 (1), pp. 11–15) mutagenesis methods which use the "PCR" technique. Methods are also known in which the mutation is introduced into the target gene in a directed manner using a synthetic oligonucleotide. This can take place either using so-called "single-strand methods" (Ausubel F. M. et al. (1987) *Current Protocols in Molecular Biology*, Green Publishing Associates) or using "double-strand methods" (Promega 1992–1993 Catalogue, 150) or using other methods as described, for example, in *Ann. Rev. Genet.* (1985) 19, pp. 423–462.

The main area of application for the CGTase according to the invention is its use for isolating γ-CD from starch. The CGTases according to the invention can be employed for this purpose using current preparation methods.

The invention consequently also relates to processes for preparing γ-CD by converting starch using a CGTase, wherein at least one CGTase according to the invention is employed as the CGTase.

Current preparation methods for producing γ-CD, in which the CGTases according to the invention can be employed in place of the CGTases which are specified in these methods, are described, for example, in:

Journal of Fermentation and Bioengineering (1990) 70 (3), pp. 190–192: The preparation of γ-CD using the β- and γ-CD-forming CGTase from Bacillus sp. AL-6 in the presence of ethanol, which results in an increased production of γ-CD.

CA 107:57466 describes the preparation of γ-CD using the γ-CGTase from Bacillus sp. 313.

EP 291,067: Preparation of γ-CD using the CGTase from *Bacillus macerans*. Product specificity for γ-CD is achieved by adding a complexing agent, for example cyclohexadec-8-en-1-one.

DE 40 09 822 (corresponds to U.S. Pat. No. 5,409,824): Production of γ-CD using the γ-CGTase from Bacillus sp. 290–3.

Both in comparison to α-CD and in comparison to β-CD, γ-CD possesses specific advantages which identify it as the only possible CD, or the most suitable CD, for a series of applications.

In comparison to α-CD, which is made of six glucose units, γ-CD, which consists of eight glucose units, possesses a larger hydrophobic cavity which also makes it possible to complex guest molecules which, for steric reasons, cannot be complexed by α-CD.

In comparison to β-CD (solubility in water at room temperature: approx. 18.5 g/l), γ-CD possesses a substantially higher solubility in water (at room temperature: approx. 232.0 g/l) and is consequently more suited than β-CD for complexing reactions in aqueous solutions. A further advantage of γ-CD, when compared with β-CD and modified β-CD derivatives, is its low toxicity. In an animal model, α-CD derivatives and β-CD derivatives are more toxic than γ-CD when administered either orally or intravenously.

In the Sequence Listing, Xxx refers to a deleted amino acid.

Other objects and features of the present invention will become apparent from the drawing and from the following Examples, which disclose the embodiments of the present invention. It should be understood, however, that the drawing and the Examples are designed for the purpose of illustration only and not as a definition of the limits of the invention.

BRIEF DESCRIPTION OF THE DRAWINGS

In the drawing,

FIG. 1 shows a comparison of the amino acid sequences of five CGTases; the conserved residues are shadowed; the eight amino acid residues underlined and in bold print are in each case relevant for modifying the product specificity;

FIG. 2 shows Bacillus sp. 1-1-CGTase from position 165 to 174: amino acid sequence from wildtype and deletion mutants;

FIG. 3 shows Thermoanaerobacter CGTase from position 171 to 180: amino acid sequence from wildtype and deletion mutants;

FIG. 4 shows sequences of oligonucleotides of Table 3 used for deletion mutagenesis in SEQ ID NOS. 30 to 37; and FIG. 5 shows sequences of oligonucleotides of Table 4 used for deletion mutagenesis in SEQ ID NOS. 42 to 44.

DETAILED DESCRIPTION OF PREFERRED EMBODIMENTS

EXAMPLE 1 Mutagenesis of the Bacillus circulans #8 (DSM 10559) CGTase

Deletion of any amino acid residues in the region, according to the invention, of amino acid residues 155–195, in particular deletion of the six amino acid residues (SEQ ID NO:5) at positions 179–184 in the β-CGTase from Bacillus circulans #8 (see Table 1; deposited Mar. 2, 1996, in the DSMZ Deutschen Sammlung von Mikroorganismen und Zellkulturen GmbH (German Collection of Microorganisms and Cell Cultures) in Mascheroder Weg 1b, D-38124 Braunschweig, Germany, under number DSM 10559 according to the Budapest Treaty), is achieved by deleting, in a manner which is known per se to a person skilled in the art, the base triplets of the CGTase structural gene which encode the corresponding amino acid residues.

For the mutagenesis, the β-CGTase gene from Bacillus circulans #8 was first of all cloned into the commercially available E. coli vector pUC19 (Boehringer, Mannheim). For this purpose, chromosomal DNA was isolated from Bacillus circulans #8 (Appl. Microbiol. Biotechnol. (1990) 33: pp. 542–546) as described in Ausubel F. M., Current Protocols In Molecular Biology, Vol. 1; Greene Publishing Associates & Wiley—Interscience, N.Y. and cleaved with the restriction endonucleases HindIII and XbaI (Boehringer, Mannheim). Fragments in a size range of between two and five kb were isolated and incubated, at 16° C. for 12 hours, together with pUC19 DNA, which had been cleaved with the restriction endonucleases HindIII and XbaI (Boehringer, Mannheim), and with T4 DNA ligase. The ligation mixture was used to transform E. coli K 12 cells which had been rendered competent for DNA uptake by means of known methods (Maniatis, Molecular Cloning, A Laboratory Manual; Cold Spring Harbor Laboratory (1982), N.Y.). The recombinant plasmid, which carries the gene for the Bacillus circulans #β-CGTase, was isolated from those E. coli cells which, following the transformation, formed starch degradation haloes on starch-containing indicator plates (Maniatis, Molecular Cloning, A Laboratory Manual; Cold Spring Harbor Laboratory (1982), N.Y., pp. 86–92).

This gene was mutagenized using the oligonucleotide-directed in vitro mutagenesis system, version 2.1, which is marketed by Amelrsham (Braunschweig) and based on a method developed by Eckstein (Nuci. Acids. Res. (1986) 14, pp. 9679–9698 and Nucl. Acids. Res. (1988) 16, pp. 791–802). The mutagenesis was carried out exactly in accordance with the protocol which is enclosed with this Amersham mutagenesis system. The method is summarized below. Details can be obtained from the protocol of this mutagenesis system.

That part of the pUC19-cloned gene for the Bacillus circulans #8 β-CGTase which encoded the region, according to the invention, from amino acid residue 155 to amino acid residue 195 of the CGTase was cloned into the commercially available vector M13 (New England Biolabs) using commercially available enzymes such as restriction endonucleases and T4 DNA ligase (Boehringer, Mannheim). A 1.6 kb AccI fragment is an example of such a fragment. This fragment was cloned into the AccI-cleaved M13 vector.

Single-stranded, recombinant M13 DNA (initial DNA) was isolated, in accordance with the experimental protocol supplied by Amersham together with the above mentioned mutagenesis system, from those E. coli host cells which had taken up the recombinant M13 vector.

For the actual mutagenesis, chemically defined mutagenesis oligonucleotides were synthesized which in each case possessed the desired sequence. Such oligonucleotides can, for example, be obtained commercially from MWG (Ebersberg). The sequence of the mutagenesis oligonucleotide was chosen such that the order of the bases in the mutagenesis oligonucleotide was inversely complementary to that part of the nucleotide sequence of the initial DNA which flanked, for 15 bases upstream and 15 bases downstream, the base triplets of the Bacillus circulans #8 β-CGTase which were contained in the initial DNA and which were to be deleted.

The sequence *of the mutagenesis oligonucleotide which was used is shown in Table 2.

TABLE 2

| 5' - (SEQ ID NO: 20) - 3' |
| --- |

Use of the mutagenesis oligonucleotide shown in Table 2 resulted in a β-CGTase gene fraction which encodes an amino acid fragment from which the six amino acid residues (SEQ ID NO:5) have been deleted.

The mutagenesis oligonucleotide was phosphorylated at its 5' end using T4 polynucleotide kinase and ATP (Amersham). The phosphorylated mutagenesis oligonucleotide was bound to the homologous regions of the initial DNA. For this, 5 μg of single-stranded initial DNA were incubated, at 70° C. for three minutes and then at 37° C. for 30 minutes, together with approximately 4 pmol of the phosphorylated mutagenesis oligonucleotide. A DNTA strand which was complementary to the initial DNA, with the exception of the nucleotides to be deleted, was then synthesized, with the mutagenesis oligonucleotide which was bound to the initial DNA serving as the starting point for the synthesis and the initial DNA serving as the template for the new synthesis of the mutated DNA strand. The synthesis itself was carried out, after adding the Klenow fragment of DNA polymerase (Amersham), a T4 DNA ligase and a nucleotide mix which contains the nucleotides DATP, dGTP and dTTP and, in place of dCTP, the thionucleotide dCTPS (Amersham), at 16° C. for 15 hours.

Remaining molecules of single-stranded initial DNA were removed from this synthesis mixture. For this, the mixture was treated with NaCl and filtered through a nitrocellulose filter (Amersham) which specifically binds single-stranded DNA. The double-stranded hybrid DNA, which remained in the flow-through, was concentrated and desalted by precipitation with EtOH. The hybrid DNA was then incubated with NciI (Amersham), a restriction endonuclease which recognizes the nucleotide sequence CC(G/C)GG but only cleaves native DNA strands and not those which contain the nucleotide analog dCTPS, at 37° C. for 90 minutes in a suitable incubation buffer (Amersham). This treatment only introduced breaks into the non-mutagenized strand (initial DNA).

The initial DNA was then removed during a 30-minute treatment, at 37° C., with exonuclease III (Amersham), which is an enzyme which degrades DNA strands starting at free ends. After the exonuclease III had been inactivated thermally (70° C. for 15 minutes), the remaining, single-stranded and mutagenized DNA strand was incubated with DNA polymerase I (Amersham), T4 DNA ligase and the nucleotides dATP, dTTP, dCTP and dGTP at 16° C. for 3 hours. This made the mutagenized single-stranded DNA into double-stranded DNA. Following a further EtOH precipitation for purification purposes, the mutagenized DNA was transformed into competent E. coli K12 cells.

The success of the mutagenesis procedure was checked by sequence analysis of the relevant region of the recombinant DNA from five clones which were obtained in the transformation. The DNA fragment which was originally cloned into M13 for the mutagenesis was excised from a vector, which was confirmed to possess a mutation, using the restriction enzymes XhoI and NdeI.

Subsequently, the corresponding, but non-mutagenized, XhoI/NdeI fragment was excised from the pUC19-based plasmid for expressing Bacillus circulans #8 β-CGTase and replaced with the mutagenized fragment using T4 DNA ligase.

EXAMPLE 2

Mutagenesis of the Bacillus sp. 1-1 β-CGTase

Between three and eight codons (subsequent and disperse) of the Bacillus sp. 1-1 β-CGTase gene encoding between three and eight amino acid residues between position 165 to 174 of the amino acid sequence of the corresponding CGTase (shown in FIG. 2) were deleted, in analogy with the method described in Example 1, using the oligonucleotides shown in Table 3 to produce eight different mutants (shown in lines 1 to 8 in Table 1).

TABLE 3

| SEQ ID NO. | LINE IN TABLE 1 | NO. OF DELETED AMINO ACIDS |
|---|---|---|
| 30 | 1 | 3 |
| 31 | 2 | 3 |
| 32 | 3 | 4 |
| 33 | 4 | 5 |
| 34 | 5 | 6 |
| 35 | 6 | 7 |
| 36 | 7 | 5 |
| 37 | 8 | 8 |

The deletion of the six subsequent codons was also introduced into a derivative of this CGTase which was described in U.S. Pat. No. 5,474,917 (=DE 4324650 A1) and whose γ-CD specificity had already been increased, as compared with that of the wild-type enxyme, by an amino acid exchange (Tyr=>Trp).

EXAMPLE 3

Mutagenesis of the Thermoanaerobacter sp. CGTase

Three different mutants (shown in Table 1 lines 12 to 14) were made as follows: Three respectively five subsequent codons respectively three disperse codons of the Thermoanaerobacter sp. CGTase gene encoding three respectively five amino acid residues between position 171 to 180 of the corresponding CGTase (see FIG. 3) were deleted in analogy with the method described in Example 1, using gonucleotides shown in Table 4.

TABLE 4

| SEQ ID NO. | LINE IN TABLE 1 | NO. OF DELETED AMINO ACIDS |
|---|---|---|
| 42 | 12 | 3 |
| 43 | 13 | 3 |
| 44 | 14 | 5 |

EXAMPLE 4

Production of Bacillus circulans #8 β-CGTase and its Derivatives According to the Invention, in E. coli The pUC19-based expression plasmids which were described in Example 1 were transformed into a secretory E. coli strain for the purpose of poducing the Bacillus circulans #8 β-CGTase and its derivative which was prepared as described in Ex. 1. E. coli WCM105 was used as the secretory E. coli strain. This strain was prepared from E. cole DS 410 as described in EP 338,410.

For the purpose of producing the Bacillus circulans #8 β-CGTase, or its derivative, therefore, E. coil WCM105 cells harboring suitable CGTase expression plasmids were incubated in LUB medium (Maniatis, *Molecular Cloning, A Laboratory Manual*; Cold Spring Harbor Laboratory (1982), N.Y.), containing 10 g/l lactose and 0.1 g/l ampicillin at 30° C. for 72 hours in a shaking water bath (revolution rate: 250 rpm). The cells were then separated off by centrifuging at 5000×g. The cell-free culture supernatant contains the β-CGTase or its derivatives.

EXAMPLE 5

Production of the Bacillus sp. 1-1 β-CGTase, and its Derivatives According to the Invention, in *E. coli*

Production was effected utilizing a procedure analogous to that described in Example 3 using the expression plasmids described in Example 2.

EXAMPLE 6

Production of the Thermoanaerobacter CGTase, and its Derivatives According to the Invention, in *E. coli*

Production was effected utilizing a procedure analogous to that described in Example 4 using the expression plasmids described in Example 3.

EXAMPLE 7

Purification of CGTases by Means of Adsorption to Carrier-bound β-cyclodextrin

CGTases are purified in a specific and mild manner by means of inity purification using SEPHAROSE®-coupled β-CD molecules.

1 g of epoxy-activated SEPHAROSE® 6B (Sigma) is washed with 3×10 ml of $H_2O$ and then with 1×5 ml of 0.1 N NaOH. The SEPHAROSE® 6B is subsequently suspended in 2 ml of a 2.8% (w/v) solution of β-CD in 0.1 N NaOH, and this suspension is incubated at 45° C. for 20 h while being shaken gently. The coupling product, consisting of β-CD and SEPHADEX® 6B, is then washed with 2×5 ml of $H_2O$. After having suspended the washed material in a 2.5% (w/v) solution of glucose in $H_2O$, the suspension is incubated at RT for 1 h in order to saturate the free coupling sites which remain. The coupling product is then washed successively with 2×5 ml of $H_2O$, 2×5 ml of 0.1 M borate buffer, pH 8.0, 2×5 ml of 0.1 M acetate buffer, pH 4.0, and 2×2 ml of 20 mM triethanolamine/Cl, pH 7.2. The coupling product is treated with 0.2 ml of 20 mM triethanolamine/Cl, pH 7.2 (final volume, approximately 2–2.5 ml) and stored until used at 4° C.

In order to specifically bind CGTases to the SEPHAROSE® 6B-coupled β-CD (CD-SEPHAROSE®), the cell-free, CGTase-containing culture supernatants which were obtained in accordance with Example 3 or 4 are treated with 0.2 ml of the CD-Sepharose and incubated at 4° C. for 1.5 h while being shaken gently. During this period, the enzyme couples to the CD-SEPHAROSE®. The enzyme/CD-SEPHAROSE® complex is isolated by centrifugation (5 min at 4000×g) and washed with 2×10 ml of 20 mM triethanolamine/Cl, pH 7.2. The CGTase enzyme is subsequently eluted by incubating the complex, at 4° C. for 1.5 h, with 2 ml of a 1% solution of β-CD in 20 mM triethanolamine/Cl, pH 7.2. After a final centrifugation (5 min at 4000×g), the supernatant containing the purified CGTase is removed.

Before characterizing the CGTases which have been purified in this way, the β-CD which is contained in the solution, and which was used for the elution, still has to be removed. To do this, a commercially obtainable PD-10 column (SEPHADEX® G-25 M; Pharmacia) is equilibrated with 35 ml of 20 mM Tris/HCl, pH 7.2 and 5 mM $CaCl_2$ (TC buffer). The β-CD-containing solution is made up to a volume of 2.5 ml with TC buffer and loaded onto the column. The column is subsequently eluted with 3.5 ml of TC buffer. The eluate which is obtained in this way contains the purified, β-CD-free CGTase.

EXAMPLE 8

Conversion of Starch into Cyclodextrins

The CGTase activities were determined using the method described in *Eur. J. Biochem.* (1990) 191, pp. 177–185.

Different quantities of a CGTase solution to be tested were incubated at 45° C., for a defined time, with a 5% solution of a soluble starch (Merck, Darmstadt) in a buffer consisting of 20 mM Tris/HCl, pH 7.2, and 5 MM $CaCl_2$. After the defined time, the reaction was terminated by adding 1.5 parts by volume of methanol. Unreacted residual starch was precipitated by incubating at 4° C. for one hour and separated off by centrifugation (10 min at 12000×g). The resulting products were determined by HPLC on a NUCLEOSIL® 10-$NH_2$ column (Macherey & Nagel, Düren), with defined cyclodextrins (Sigma, Munich) serving as standards. One unit (1 U) is defined as the quantity of enzyme which forms 1 μM of cyclodextrins per minute from starch under the conditions described.

EXAMPLE 9

Determination of the Specific Total CGTase Activities of Purified CGTases

The specific total CGTase activity of purified CGTases is defined as the volume activity per quantity of protein (U/mg).

The CGTase volume activity (U/ml) of an enzyme sample is determined as described in Example 8.

The protein content (mg/ml) of a solution of the purified CGTase is determined-using the method described by M. Bradford (*Anal. Biochem.* (1976) 72, pp. 248 ff). The chemicals which are required for this purpose are obtained from Bio-Rad.

The following specific total CGTase activities (spec. activity) were determined for the *Bacillus Circulans* #8, Bacillus sp. 1-1 and the Thermoanaerobacter sp. CGTases and the deletion mutants which were produced (as described in Example 1, Example 2, and Example 3) from them:

| Enzyme | Line in Table 1 | Rel. activity (%) | Spec. activity (U/mg) |
|---|---|---|---|
| Wild-type CGTase from *Bacillus circulans* #8 | — | 100 | 106 |
| Mutant with 6 amino acids deleted, derived from it | 10 | 77 | 82 |
| Wild-type CGTase from Bacillus sp. 1-1 | — | 100 | 120 |
| Mutant with 3 subsequent amino acids deleted, derived from it | 1 | 62 | 74 |
| Mutant with 3 disperse amino acids deleted, derived from it | 2 | 66 | 79 |
| Mutant with 4 amino acids deleted, derived from it | 3 | 68 | 82 |
| Mutant with 5 subsequent amino acids deleted, derived from it | 4 | 73 | 88 |
| Mutant with 6 amino acids deleted, derived from it | 5 | 65 | 78 |
| Mutant with 7 amino acids deleted, derived from it | 6 | 62 | 74 |
| Mutant with 5 disperse amino acids deleted, derived from it | 7 | 63 | 76 |
| Mutant with 8 amino acids deleted, derived from it | 8 | 82 | 98 |
| Mutated derivative (Tyr => Trp) of Bacillus sp. 1-1 CGTase | — | 100 | 23 |
| Mutant with 6 amino acids deleted, derived from it | 5 | 73 | 17 |
| Wild-type CGTase from Thermoanaerobacter sp. | — | 100 | 168 |
| Mutant with 3 subsequent amino acids deleted, derived from it | 12 | 65 | 109 |
| Mutant with 3 disperse amino acids deleted, derived from it | 13 | 68 | 114 |
| Mutant with 5 subsequent amino acids deleted, derived from it | 14 | 66 | 111 |

Deletions from three to eight amino acid residues (subsequent or disperse) always result in enzymes with more than 60% residual activity in comparison to the respective wildtype enzymes.

EXAMPLE 10

Conversion of Starch Using the Non-mutagenized CGTases from *Bacillus circulans* #8, Bacillus sp. 1-1 and Thermoanaerobacter sp. and the Derivatives Prepared as Described in Examples 4, 5, and 6

In order to compare the product spectra of the non-mutagenized CGTases with those of the derivatives which were in each case obtained from them by deletion mutagenesis, as described in Examples 1, 2, and 3, identical enzyme activities were employed for converting the starch (Example 8). At defined times, the product composition was investigated as described. The following results were obtained:

| Enzyme | Line in Table 1 | $\gamma/\alpha+\beta$ |
|---|---|---|
| Wild-type CGTase from *Bacillus circulans* #8 | — | 0.19 |
| Mutant with 6 amino acids deleted, derived from it | 10 | 0.46 |
| Wild-type CGTase from Bacillus sp. 1-1 | — | 0.14 |
| Mutant with 3 subsequent amino acids deleted, derived from it | 1 | 0.44 |
| Mutant with 3 disperse amino acids deleted, derived from it | 2 | 0.52 |
| Mutant with 4 amino acids deleted, derived from it | 3 | 0.63 |
| Mutant with 5 subsequent amino acids deleted, derived from it | 4 | 0.84 |
| Mutant with 6 amino acids deleted, derived from it | 5 | 0.47 |
| Mutant with 7 amino acids deleted, derived from it | 6 | 0.46 |
| Mutant with 5 disperse amino acids deleted, derived from it | 7 | 0.67 |
| Mutant with 8 amino acids deleted, derived from it | 8 | 0.25 |
| Mutated derivative (Tyr => Trp) of Bacillus sp. 1-1 CGTase | — | 2.23 |
| Mutant with 6 amino acids deleted, derived from it | 5 | 3.54 |
| Wild-type CGTase from Thermoanaerobacter sp. | — | 0.17 |
| Mutant with 3 subsequent amino acids deleted, derived from it | 12 | 0.31 |
| Mutant with 3 disperse amino acids deleted, derived from it | 13 | 0.27 |
| Mutant with 5 subsequent amino acids deleted, derived from it | 14 | 0.39 |

In any enzyme mutated by the deletion of between three and eight amino acid residues (subsequent or disperse), the γ-CD forming activity of the respective enzymes could be significantly improved. The maximum effect could be obtained by the deletion of five amino acid residues.

| COMPARISON 1: *BACILLUS CIRCULANS* #8 | | | | | | | |
|---|---|---|---|---|---|---|---|
| Wild-Type CGTase | | | | Deletion mutant of this | | | |
| Time (min) | α – CD (%) | β – CD (%) | γ – CD (%) | γ/(α + β) | α – CD (%) | β – CD (%) | γ – CD (%) | γ/(α + β) |
| 5 | 13 | 70 | 17 | 0.2 | 9 | 58.0 | 33 | 0.49 |
| 10 | 13.5 | 70.3 | 16.2 | 0.19 | 8.2 | 60.5 | 31.3 | 0.46 |
| 15 | 11.7 | 66.3 | 22.0 | 0.28 | 9.4 | 62.0 | 28.6 | 0.40 |

| COMPARISON 2: BACILLUS SP. 1-1 | | | | | | | |
|---|---|---|---|---|---|---|---|
| Wild-Type CGTase | | | | Deletion mutant of this | | | |
| Time (min) | α – CD (%) | β – CD (%) | γ – CD (%) | γ/(α + β) | α – CD (%) | β – CD (%) | γ – CD (%) | γ/(α + β) |
| A) | | | | | | | | |
| 5 | 0 | 100 | 0 | 0 | 68 | 32 | 33 | 0.47 |
| 10 | 0 | 88 | 12 | 0.14 | 0 | 68 | 32 | 0.47 |
| 15 | 0 | 88 | 12 | 0.14 | 0 | 67.7 | 32.3 | 0.48 |
| B) | | | | | | | | |
| 5 | 0 | 27 | 73 | 2.7 | 0 | 0 | 100 | — |
| 10 | 0 | 31 | 69 | 2.23 | 0 | 22 | 78 | 3.54 |
| 15 | 0 | 32.5 | 67.5 | 2.08 | 0 | 16.6 | 83.4 | 5.02 |

While several embodiments of the present invention have been shown and described, it is to be understood that many changes and modifications may be made there unto without departing from the spirit and scope of the invention as defined in the appended claims.

What is claimed is:

1. A cyclodextrin glycosyltransferase (CGTase) protein which converts starch substrates to cyclodextrin (CD) produces γ-CD to an increased extent relative to the wild-type and which still exhibits at least 60% of specific total γ-CGTase activity of a starting CGTase which was used for preparing it, comprising an amino acid sequence which differs from the amino acid sequences of the CGTases specified in FIG. 1 by the deletion of the amino acid residues which are in each case printed in bold in FIG. 1 and is selected from the group described in Table 1 consisting of
(SEQ ID NO:6) deleted from (SEQ ID NO:1);
(SEQ ID NO:7; Glu Xaa Asn Xaa Asn) deleted from (SEQ ID NO:1);
(SEQ ID NO:8) deleted from (SEQ ID NO:1);
(SEQ ID NO:9) deleted from (SEQ ID NO:1);
(SEQ ID NO:10) deleted from (SEQ ID NO:1);
(SEQ ID NO:11) deleted from (SEQ ID NO:1);
(SEQ ID NO:12; Ala Xaa Glu Xaa Asn Xaa Asn Tyr) deleted from (SEQ ID NO: );
(SEQ ID No:13) deleted from (SEQ ID NO:1);
(SEQ ID NO:14) deleted from (SEQ ID NO:2);
(SEQ ID NO:15) deleted from (SEQ ID NO:3);
(SEQ ID NO:16) deleted from (SEQ ID NO:4);
(SEQ TO NO:17) deleted from (SEQ ID NO:5);
(SEQ ID NO:11; Glu Xaa Asp Xaa Thr) deleted from (SEQ ID NO:5) and
(SEQ ID NO:19) deleted from (SEQ ID NO:5),
wherein Xaa indicates no deletion of that amino acid residue from the starting CGTase, and
where the remaining amino acid sequence of the CGTase is homologous to the amino acid sequence of the CGTase from the microorganism which is in each case specified in FIG. 1 to the extent that the sequence exhibits CGTase activity without said deletion.

2. A cyclodextrin gylcosyltransferase (CGTase) protein which converts starch substrates to cyclodextrin (CD), produces γ-CD to an increased extent relative to the wild-type and which still exhibits at least 60% of specific total γ-CGTase activity of a starting CGTase which was used for preparing it, comprising CGTase from Bacillus sp. 1-1 having an amino acid sequence differing from the amino acid sequence of starting CGTase by deletion of between three and eight amino acids in a region from amino acid position 165 up to and including amino acid position 174 of (SEQ ID NO:21) as shown in FIG. 2; and where position 1 of protein sequence is the beginning of a signal peptide for the CGTase and deletion brings about an increase in the γ-CGTase activity of the protein.

3. A cyclodextrin gylcosyltransferase (CGTase) protein which converts starch substrates to cyclodextrin (CD), produces γ-CD to an increased extent relative to the wild-type and which still exhibits at least 60% of specific total γ-CGTase activity of a starting CGTase which was used for preparing it, comprising CGTase from Thermo anaerobacter having an amino acid sequence differing from the amino acid sequence of starting CGTase by deletion of between three and five amino acids in a region from amino acid position 171 up to and including amino acid position 180 of (SEQ ID NO:38) as shown in FIG. 3; and where position 1 of protein sequence is the beginning of a signal peptide for the CGTase and deletion brings about an increase in the γ-CGTase activity of the protein.

4. A process for preparing γ-CD by converting starch using CGTase, the improvement comprising utilizing CGTase of claim 1.

5. A process for preparing γ-CD by converting starch using CGTase, the improvement comprising utilizing CGTase of claim 2.

6. A process for preparing γ-CD by converting starch using CGTase, the improvement comprising utilizing CGTase of claim 3.

* * * * *

UNITED STATES PATENT AND TRADEMARK OFFICE
CERTIFICATE OF CORRECTION

PATENT NO. : 6,472,192 B1
DATED : October 29, 2002
INVENTOR(S) : Schulz et al.

It is certified that error appears in the above-identified patent and that said Letters Patent is hereby corrected as shown below:

<u>Title page</u>,
Item [75], please add the following inventors:
-- Anton Candussio, München, Germany;
  Günter Wich, München, Germany --

Signed and Sealed this

Tenth Day of February, 2004

JON W. DUDAS
*Acting Director of the United States Patent and Trademark Office*

SEQUENCE LISTING

<160> NUMBER OF SEQ ID NOS: 44

<210> SEQ ID NO 1
<211> LENGTH: 100
<212> TYPE: PRT
<213> ORGANISM: Bacillus sp. 1-1

<400> SEQUENCE: 1

```
His Gly Tyr Trp Ala Arg Asp Tyr Lys Lys Thr Asn Pro Tyr Tyr Gly
  1               5                  10                  15

Asn Phe Asp Asp Phe Asp Arg Leu Met Ser Thr Ala His Ser Asn Gly
                 20                  25                  30

Ile Lys Val Ile Met Asp Phe Thr Pro Asn His Ser Ser Pro Ala Leu
             35                  40                  45

Glu Thr Asn Pro Asn Tyr Val Glu Asn Gly Ala Ile Tyr Asp Asn Gly
         50                  55                  60

Ala Leu Leu Gly Asn Tyr Ser Asn Asp Gln Gln Asn Leu Phe His His
 65                  70                  75                  80

Asn Gly Gly Thr Asn Phe Ser Ser Tyr Glu Asp Ser Ile Tyr Arg Asn
                 85                  90                  95

Leu Tyr Asp Leu
            100
```

<210> SEQ ID NO 2

-continued

```
<211> LENGTH: 100
<212> TYPE: PRT
<213> ORGANISM: Bacillus ohbensis

<400> SEQUENCE: 2

His Gly Tyr Trp Ala Arg Asp Tyr Lys Arg Thr Asn Pro Phe Tyr Gly
 1               5                  10                  15

Asp Phe Ser Asp Phe Asp Arg Leu Met Asp Thr Ala His Ser Asn Gly
            20                  25                  30

Ile Lys Val Ile Met Asp Phe Thr Pro Asn His Ser Ser Pro Ala Leu
        35                  40                  45

Glu Thr Asp Pro Ser Tyr Ala Glu Asn Gly Ala Val Tyr Asn Asp Gly
    50                  55                  60

Val Leu Ile Gly Asn Tyr Ser Asn Asp Pro Asn Asn Leu Phe His His
65                  70                  75                  80

Asn Gly Gly Thr Asn Phe Ser Ser Tyr Glu Asp Ser Ile Tyr Arg Asn
                85                  90                  95

Leu Tyr Asp Leu
            100

<210> SEQ ID NO 3
<211> LENGTH: 100
<212> TYPE: PRT
<213> ORGANISM: Bacillus circulans

<400> SEQUENCE: 3

His Gly Tyr Trp Ala Arg Asp Phe Lys Lys Thr Asn Pro Tyr Phe Gly
 1               5                  10                  15

Thr Met Ala Asp Phe Gln Asn Leu Ile Thr Thr Ala His Ala Lys Gly
            20                  25                  30

Ile Lys Ile Val Ile Asp Phe Ala Pro Asn His Thr Ser Pro Ala Met
        35                  40                  45

Glu Thr Asp Thr Ser Phe Ala Glu Asn Gly Arg Leu Tyr Asp Asn Gly
    50                  55                  60

Thr Leu Val Gly Gly Tyr Thr Asn Asp Thr Asn Gly Tyr Phe His His
65                  70                  75                  80

Asn Gly Gly Ser Asn Phe Ser Ser Leu Glu Asn Gly Ile Tyr Lys Asn
                85                  90                  95

Leu Tyr Asp Leu
            100

<210> SEQ ID NO 4
<211> LENGTH: 100
<212> TYPE: PRT
<213> ORGANISM: Paenibacillus macerans

<400> SEQUENCE: 4

His Gly Tyr Trp Ala Arg Asp Phe Lys Gln Thr Asn Asp Ala Phe Gly
 1               5                  10                  15

Asp Phe Ala Asp Phe Gln Asn Leu Ile Asp Thr Ala His Ala His Asn
            20                  25                  30

Ile Lys Val Val Ile Asp Phe Ala Pro Asn His Thr Ser Pro Ala Asp
        35                  40                  45

Arg Asp Asn Pro Gly Phe Ala Glu Asn Gly Gly Met Tyr Asp Asn Gly
    50                  55                  60

Ser Leu Leu Gly Ala Tyr Ser Asn Asp Thr Ala Gly Leu Phe His His
65                  70                  75                  80
```

-continued

Asn Gly Gly Thr Asn Phe Ser Thr Ile Glu Asp Gly Ile Tyr Lys Asn
                85                  90                  95

Leu Tyr Asp Leu
            100

<210> SEQ ID NO 5
<211> LENGTH: 100
<212> TYPE: PRT
<213> ORGANISM: Thermoanaerobacter sp.

<400> SEQUENCE: 5

His Gly Tyr Trp Ala Arg Asp Phe Lys Lys Thr Asn Pro Phe Phe Gly
 1               5                  10                  15

Ser Phe Thr Asp Phe Gln Asn Leu Ile Ala Thr Ala His Ala His Asn
                20                  25                  30

Ile Lys Val Ile Ile Asp Phe Ala Pro Asn His Thr Ser Pro Ala Ser
            35                  40                  45

Glu Thr Asp Pro Thr Tyr Gly Glu Asn Gly Arg Leu Tyr Asp Asn Gly
        50                  55                  60

Val Leu Leu Gly Gly Tyr Thr Asn Asp Thr Asn Gly Tyr Phe His His
 65                  70                  75                  80

Tyr Gly Gly Thr Asn Phe Ser Ser Tyr Glu Asp Gly Ile Tyr Arg Asn
                85                  90                  95

Leu Phe Asp Leu
            100

<210> SEQ ID NO 6
<211> LENGTH: 3
<212> TYPE: PRT
<213> ORGANISM: Bacillus sp. 1-1

<400> SEQUENCE: 6

Thr Asn Pro
 1

<210> SEQ ID NO 7
<211> LENGTH: 3
<212> TYPE: PRT
<213> ORGANISM: Bacillus sp. 1-1

<400> SEQUENCE: 7

Glu Asn Asn
 1

<210> SEQ ID NO 8
<211> LENGTH: 4
<212> TYPE: PRT
<213> ORGANISM: Bacillus sp. 1-1

<400> SEQUENCE: 8

Glu Thr Asn Pro
 1

<210> SEQ ID NO 9
<211> LENGTH: 5
<212> TYPE: PRT
<213> ORGANISM: Bacillus sp. 1-1

<400> SEQUENCE: 9

Glu Thr Asn Pro Asn
 1               5

<210> SEQ ID NO 10
<211> LENGTH: 6
<212> TYPE: PRT
<213> ORGANISM: Bacillus sp. 1-1

<400> SEQUENCE: 10

Leu Glu Thr Asn Pro Asn
 1               5

<210> SEQ ID NO 11
<211> LENGTH: 7
<212> TYPE: PRT
<213> ORGANISM: Bacillus sp. 1-1

<400> SEQUENCE: 11

Leu Glu Thr Asn Pro Asn Tyr
 1               5

<210> SEQ ID NO 12
<211> LENGTH: 5
<212> TYPE: PRT
<213> ORGANISM: Bacillus sp. 1-1

<400> SEQUENCE: 12

Ala Glu Asn Asn Tyr
 1               5

<210> SEQ ID NO 13
<211> LENGTH: 8
<212> TYPE: PRT
<213> ORGANISM: Bacillus sp. 1-1

<400> SEQUENCE: 13

Ala Leu Glu Thr Asn Pro Asn Tyr
 1               5

<210> SEQ ID NO 14
<211> LENGTH: 6
<212> TYPE: PRT
<213> ORGANISM: Bacillus ohbensis

<400> SEQUENCE: 14

Leu Glu Thr Asp Pro Ser
 1               5

<210> SEQ ID NO 15
<211> LENGTH: 6
<212> TYPE: PRT
<213> ORGANISM: Bacillus circulans

<400> SEQUENCE: 15

Met Glu Thr Asp Thr Ser
 1               5

<210> SEQ ID NO 16
<211> LENGTH: 6
<212> TYPE: PRT
<213> ORGANISM: Paenibacillus macerans

<400> SEQUENCE: 16

Asp Arg Asp Asn Pro Gly
 1               5

<210> SEQ ID NO 17

```
<211> LENGTH: 3
<212> TYPE: PRT
<213> ORGANISM: Thermoanaerobacter sp.

<400> SEQUENCE: 17

Thr Asp Pro
  1

<210> SEQ ID NO 18
<211> LENGTH: 3
<212> TYPE: PRT
<213> ORGANISM: Thermoanaerobacter sp.

<400> SEQUENCE: 18

Glu Asp Thr
  1

<210> SEQ ID NO 19
<211> LENGTH: 5
<212> TYPE: PRT
<213> ORGANISM: Thermoanaerobacter sp.

<400> SEQUENCE: 19

Glu Thr Asp Pro Thr
  1               5

<210> SEQ ID NO 20
<211> LENGTH: 30
<212> TYPE: DNA
<213> ORGANISM: Bacillus sp. 1-1

<400> SEQUENCE: 20
cacacctctc cagcgtttgc cgaaaatggc                                    30

<210> SEQ ID NO 21
<211> LENGTH: 10
<212> TYPE: PRT
<213> ORGANISM: Bacillus sp. 1-1

<400> SEQUENCE: 21

Pro Ala Leu Glu Thr Asn Pro Asn Tyr Val
  1               5                  10

<210> SEQ ID NO 22
<211> LENGTH: 7
<212> TYPE: PRT
<213> ORGANISM: Bacillus sp. 1-1

<400> SEQUENCE: 22

Pro Ala Leu Glu Asn Tyr Val
  1               5

<210> SEQ ID NO 23
<211> LENGTH: 7
<212> TYPE: PRT
<213> ORGANISM: Bacillus sp. 1-1

<400> SEQUENCE: 23

Pro Ala Leu Thr Pro Tyr Val
  1               5

<210> SEQ ID NO 24
<211> LENGTH: 6
<212> TYPE: PRT
<213> ORGANISM: Bacillus sp. 1-1
```

<400> SEQUENCE: 24

Pro Ala Leu Asn Tyr Val
 1               5

<210> SEQ ID NO 25
<211> LENGTH: 5
<212> TYPE: PRT
<213> ORGANISM: Bacillus sp. 1-1

<400> SEQUENCE: 25

Pro Ala Leu Tyr Val
 1               5

<210> SEQ ID NO 26
<211> LENGTH: 4
<212> TYPE: PRT
<213> ORGANISM: Bacillus sp. 1-1

<400> SEQUENCE: 26

Pro Ala Tyr Val
 1

<210> SEQ ID NO 27
<211> LENGTH: 3
<212> TYPE: PRT
<213> ORGANISM: Bacillus sp. 1-1

<400> SEQUENCE: 27

Pro Ala Val
 1

<210> SEQ ID NO 28
<211> LENGTH: 5
<212> TYPE: PRT
<213> ORGANISM: Bacillus sp. 1-1

<400> SEQUENCE: 28

Pro Leu Thr Pro Val
 1               5

<210> SEQ ID NO 29
<211> LENGTH: 2
<212> TYPE: PRT
<213> ORGANISM: Bacillus sp. 1-1

<400> SEQUENCE: 29

Pro Val
 1

<210> SEQ ID NO 30
<211> LENGTH: 30
<212> TYPE: DNA
<213> ORGANISM: Bacillus sp. 1-1

<400> SEQUENCE: 30
tcaccggcac ttgaaaacta tgttgaaaat                               30

<210> SEQ ID NO 31
<211> LENGTH: 30
<212> TYPE: DNA
<213> ORGANISM: Bacillus sp. 1-1

<400> SEQUENCE: 31
tcaccggcac ttacgcctta tgttgaaaat                                      30

<210> SEQ ID NO 32
<211> LENGTH: 30
<212> TYPE: DNA
<213> ORGANISM: Bacillus sp. 1-1

<400> SEQUENCE: 32
tcatcaccgg cacttaacta tgttgaaaat                                      30

<210> SEQ ID NO 33
<211> LENGTH: 30
<212> TYPE: DNA
<213> ORGANISM: Bacillus sp. 1-1

<400> SEQUENCE: 33
tcatcaccgg cactttatgt tgaaaatggg                                      30

<210> SEQ ID NO 34
<211> LENGTH: 30
<212> TYPE: DNA
<213> ORGANISM: Bacillus sp. 1-1

<400> SEQUENCE: 34
cattcatcac cggcatatgt tgaaaatggg                                      30

<210> SEQ ID NO 35
<211> LENGTH: 30
<212> TYPE: DNA
<213> ORGANISM: Bacillus sp. 1-1

<400> SEQUENCE: 35
cattcatcac cggcagttga aaatggggcg                                      30

<210> SEQ ID NO 36
<211> LENGTH: 30
<212> TYPE: DNA
<213> ORGANISM: Bacillus sp. 1-1

<400> SEQUENCE: 36
tcatcaccgc ttacgcctgt tgaaaatggg                                      30

<210> SEQ ID NO 37
<211> LENGTH: 30
<212> TYPE: DNA
<213> ORGANISM: Bacillus sp. 1-1

<400> SEQUENCE: 37
aatcattcat caccggttga aaatggggcg                                      30

<210> SEQ ID NO 38
<211> LENGTH: 10
<212> TYPE: PRT
<213> ORGANISM: Thermoanaerobacter sp.

<400> SEQUENCE: 38

Pro Ala Ser Glu Thr Asp Pro Thr Tyr Gly
 1               5                  10

<210> SEQ ID NO 39
<211> LENGTH: 7
<212> TYPE: PRT
<213> ORGANISM: Thermoanaerobacter sp.

```
<400> SEQUENCE: 39

Pro Ala Ser Glu Thr Tyr Gly
 1               5

<210> SEQ ID NO 40
<211> LENGTH: 7
<212> TYPE: PRT
<213> ORGANISM: Thermoanaerobacter sp.

<400> SEQUENCE: 40

Pro Ala Ser Thr Pro Tyr Gly
 1               5

<210> SEQ ID NO 41
<211> LENGTH: 5
<212> TYPE: PRT
<213> ORGANISM: Thermoanaerobacter sp.

<400> SEQUENCE: 41

Pro Ala Ser Tyr Gly
 1               5

<210> SEQ ID NO 42
<211> LENGTH: 30
<212> TYPE: DNA
<213> ORGANISM: Bacillus sp. 1-1

<400> SEQUENCE: 42
tctcctgcat cagagaccta tggggaaaat                                    30

<210> SEQ ID NO 43
<211> LENGTH: 30
<212> TYPE: DNA
<213> ORGANISM: Bacillus sp. 1-1

<400> SEQUENCE: 43
tctcctgcat caacacctta tggggaaaat                                    30

<210> SEQ ID NO 44
<211> LENGTH: 30
<212> TYPE: DNA
<213> ORGANISM: Bacillus sp. 1-1

<400> SEQUENCE: 44
acatctcctg catcatatgg ggaaaatggt                                    30
```